United States Patent [19]

Rynbrandt et al.

[11] 4,168,315
[45] Sep. 18, 1979

[54] DIANISYL THIAZOLE COMPOUND, COMPOSITIONS AND METHOD OF ANTITHROMBOTIC TREATMENT

[75] Inventors: Ronald H. Rynbrandt, Portage; Edward E. Nishizawa, Schoolcraft Township, Kalamazoo County, both of Mich.

[73] Assignee: The Upjohn Company, Kalamazoo, Mich.

[21] Appl. No.: 837,083

[22] Filed: Sep. 28, 1977

[51] Int. Cl.² .......................................... C07D 277/20
[52] U.S. Cl. .................................. 424/270; 548/202; 548/203; 548/204; 544/133; 544/369; 546/209; 424/248.57
[58] Field of Search .................... 260/302 R; 544/133, 544/369; 546/209; 424/248.57, 270

[56] References Cited

U.S. PATENT DOCUMENTS

| | | | |
|---|---|---|---|
| 3,458,526 | 7/1969 | Lednicer | 260/302 R |
| 3,506,679 | 4/1970 | Cavalla et al. | 260/302 R |
| 3,558,644 | 1/1971 | Lednicer | 260/302 R |

*Primary Examiner*—Nicholas S. Rizzo
*Attorney, Agent, or Firm*—John J. Killinger; Roman Salinwanchik

[57] ABSTRACT

Novel compounds of Formula I:

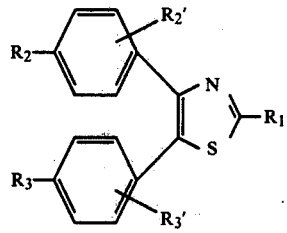

Formula I in association with a pharmaceutical carrier. The compositions are useful in vitro and in vivo for reduction of platelet adhesiveness and inhibition of platelet aggregation and preventing or treating disease conditions resulting from increased platelet adhesiveness or platelet aggregation.

18 Claims, No Drawings

4,168,315

DIANISYL THIAZOLE COMPOUND, COMPOSITIONS AND METHOD OF ANTITHROMBOTIC TREATMENT

BACKGROUND OF THE INVENTION

The following prior art was considered in preparing the patent application: U.S. Pat. No. 3,707,475; U.S. Pat. No. 3,560,514; U.S. Pat. No. 3,558,644; J. G. Lombardino and E. H. Wiseman, *J. Med. Chem.* 17:1182 (1974) and E. H. Wiseman, H. M. McIllhenny and J. W. Bettes, *J. Pharm. Sci.* 64:1469 (1975).

BRIEF DESCRIPTION OF THE INVENTION

This invention relates to novel compounds of the Formula I and to a broader group of compounds, Formula II, which are useful in association with a pharmaceutical carrier for the in vitro and in vivo inhibition of platelet adhesiveness and platelet aggregation and prevention or treatment of diseases arising from platelet adhesiveness and platelet aggregation.

DETAILED DESCRIPTION OF THE INVENTION

Novel compounds of the formula:

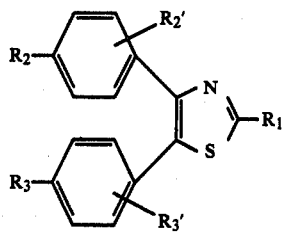

Formula I wherein $R_2$ and $R_3$ are the same or different, and are selected from the group consisting of hydrogen, fluorine, chlorine, bromine, trifluoromethyl, alkoxy or from one to four carbon atoms, inclusive, thioalkoxy of from one to four carbon atoms, inclusive, and alkyl or from one to four carbon atoms, inclusive; $R_{2'}$ and $R_{3'}$ are the same or different and are chosen from the group consisting of hydrogen and alkoxy from one to four carbon atoms, inclusive, with the proviso that when $R_{2'}$ is alkoxy, then $R_2 = R_{2'}$ and when $R_{3'}$ is alkoxy then $R_3 = R_{3'}$; $R_1$ is selected from the group consisting of hydrogen; trifluoromethyl;

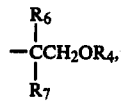

where $R_4$ is hydrogen, alkyl of one to four carbon atoms, inclusive, or

where $R_5$ is alkyl of one to six carbon atoms, inclusive, $R_6$ and $R_7$ are the same or different and are chosen from the group consisting of hydrogen and alkyl of one to three carbon atoms;

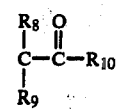

where $R_8$ and $R_9$ are the same or different and are chosen from the group consisting of alkyl from one to three carbon atoms, inclusive, $R_{10}$ is alkoxy of from one to three carbon atoms, inclusive,

where $R_{11}$ and $R_{12}$ are the same or different and are chosen from the group consisting of hydrogen, alkyl of from one to six carbon atoms, inclusive, hydroxyalkyl of from one to six carbon atoms, inclusive, cycloalkyl of from five to seven carbon atoms, inclusive, or taken together with the nitrogen atom to which they are attached,

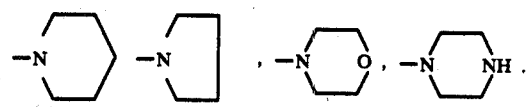

The compounds of this invention are prepared from readily available starting materials using chemical reactions that are well known in the art. For example, the requisite α-bromoketones, e.g., 4 in Scheme I, may be prepared as outlined by Wagner et al., "Synthetic Organic Chemistry," J. Wiley & Sons, Inc., New York, N.Y., 1958, page 100. The ketones, e.g., 3 in Scheme I are prepared by the methods outlined by Gore in "Friedel Crafts and Related Reactions," G. Olah, ed., Vol. III, Interscience Publishers, New York, N.Y. 1964, Chapter 31. As indicated in Scheme I, an appropriately substituted phenylacetic acid (1) is converted to the corresponding acid chloride (2) by reacting the acid with an excess of thionyl chloride for 1 to 5 hours at reflux.

SCHEME I

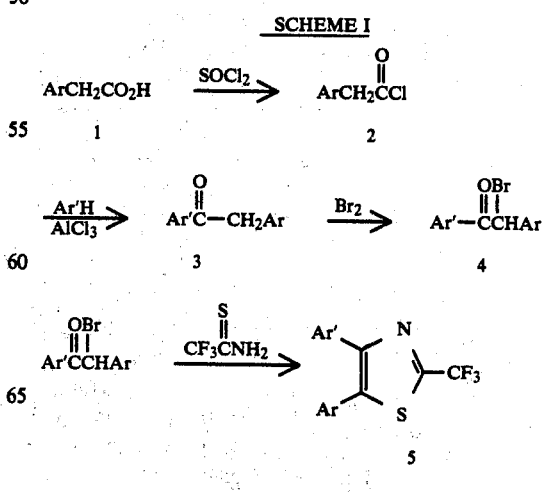

-continued
SCHEME I

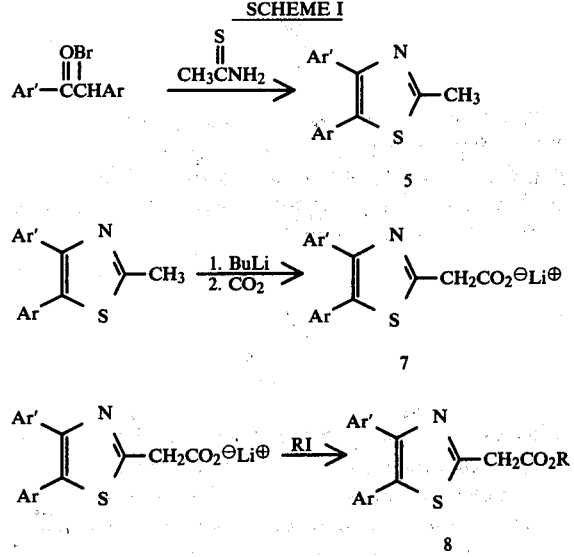

Residual thionyl chloride is removed by distillation and the crude product (2) is used directly in the next step. The Friedel-Crafts acylation is run either neat, allowing the aromatic substrate to serve also as solvent, or in an inert solvent such as chloroform, methylene chloride, carbon tetrachloride, carbon disulfide, benzene and the like. The reaction temperature varies from ambient to the reflux temperature of the solvent and the duration of the reaction may be from about one hour to several days. The reaction is run in the presence of a Lewis acid such as AlCl₃, SnCl₄ and the like. After work-up, the crude substituted 2-aryl acetophenone, 3, is purified by distillation, crystallization, or chromatography.

The ketone 3 is brominated by reaction with reagent grade molecular bromine in an inert solvent such as chloroform, carbon tetrachloride, mixtures of choroform-ether, carbon tetrachloride-ether, and the like. The reaction is run for periods ranging from 0.5 to 5 hours at temperatures ranging from 10° to the reflux temperature of the solvent. Product 4 may be purified by standard techniques.

Thiazoles 5 and 6 are obtained by reacting the appropriate bromoketone 4 with the appropriate thioamide. The two reactants are heated in an inert organic solvent such as methanol, ethanol, propanol, acetonitrile and the like. More specifically, the reactants are used in molar ratios of 4 to thioamide ranging from 1:1 to 1:5, and the reaction, when carried out at reflux temperature needs for completion between 1 and 24 hours. It is possible to carry out the reaction at lower temperatures within longer reaction periods. In a preferred variation for the preparation of 5, trifluorothioacetamide is prepared in situ by refluxing trifluoroacetamide with pulverized phosphorus pentasulfide in benzene, toluene or the like for about 4 days followed by direct addition of bromoketone 4. The mixture is then refluxed for an additional 1 to 24 hours. The desired product is recovered in a conventional manner which includes saponification of residual thioamide and removal of the solvent by distillation or precipitating the product by diluting the solvent with water or with another solvent in which the desired product is insoluble. The product can be purified by crystallization or chromatography.

In the event a 4,5-diaryl-2-thiazoleacetic acid derivative such as 7 or 8 is desired, a 2-alkyl-4,5-diarylthiazole such as 6 is reacted with n-butyllithium at low temperatures in an inert organic solvent. Generally the thiazole reactant is in solution, e.g., in tetrahydrofuran, ether, dibutyl ether, or the like, whereas the n-butyl-lithium is in a hydrocarbon solvent which does not solidify at the temperature of the reaction (−25° to −80° C.), e.g., petroleum ether, n-pentane, n-hexane or the like. To the carbanion thus formed is added powdered carbon dioxide over a period of several minutes in order to form the carbonated product. The reaction mixture may then be warmed, concentrated, and the crude lithium salt may be isolated by filtration after slurring with ether. It may be purified by recrystallization from a solvent of appropriate polarity such as acetone.

Salt 7 may be reacted with an appropriate alkylating agent, e.g., methyl iodide, to give the corresponding esters (8). The reaction is conveniently run at temperatures between ambient and the reflux temperature of the reaction mixture in a suitable solvent such as dimethylformamide for from several hours to 2 days. When reaction is complete, the reaction mixture is made aqueous and the product is extracted with a suitable organic solvent such as ether, chloroform, methylene chloride, and the like. The product may be purified by conventional means such as chromatography or crystallization.

With reference to Scheme II, esters, e.g., 8, may be saponified with an appropriate alkali such as sodium hydroxide, potassium hydroxide, and the like to give the corresponding salt 9. The ester is reacted with an equimolar amount of the above alkali metal hydroxides in aqueous-methanolic medium. Reaction conditions are not critical. The reaction is conveniently run at ambient temperature for from several hours to several days and the product is purified by removal of solvent and liberated alcohol in vacuo.

Esters 8 may be converted to amides 10 using standard reaction conditions by reacting an excess of a primary or secondary amine with the ester in solvents such as methanol, dimethylsulfoxide, dimethylformamide, and the like at temperatures ranging from −30° to ambient temperature or greater for periods of several minutes to several days. The product may be purified by standard methods such as chromatography and the like.

SCHEME II

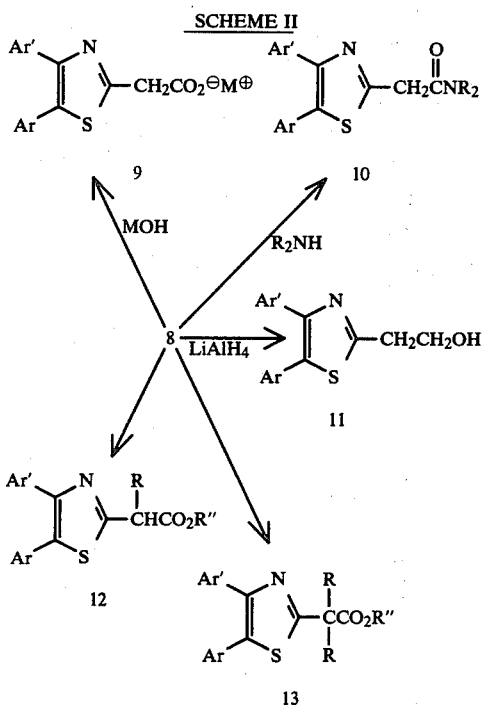

Esters 8 may also be converted to the corresponding alcohols 11 by reaction with an excess of lithium aluminum hydride in an inert solvent such as ether, tetrahydrofuran and the like. Temperatures are generally held at room temperature or below. The product is purified by standard means.

Esters 8 may be alkylated at the α-carbon using standard techniques. The ester is first reacted with a slight molar excess of strong base such as lithium diisopropyl amide or the like in an inert solvent such as tetrahydrofuran or the like. The reaction is run by slow addition of the ester to the base maintaining the reaction temperature at −80° to −60°, followed by stirring for one to two hours. The alkylating agent, e.g., alkyl iodide, bromide, or the like, is then added to the reaction mixture, and the mixture is stirred for up to one hour, allowed to warm to ambient temperature and worked up in a standard manner. The product may be purified by chromatography, crystallization and the like. In the alkylation procedure control of the desired product, 12 or 13 is determined by the amount of alkylating agent used, 12 predominating when up to one equivalent is used and 13 predominating when more than two equivalents are used.

In the manner described above, esters 12 and 13 may be hydrolyzed to the corresponding salts with alkali, reacted with amines to give the corresponding amides, or reduced with metal hydrides to give the corresponding alcohols.

EXAMPLE 1

2-Trifluormethyl-4,5-bis(p-methoxyphenyl)thiazole

Part A — Trifluoroacetamidine

Using a modification of the procedure of Reilly & Brown, W. L. Reilly and H. C. Brown, *J. Am. Chem. Soc.*, 78, 6032 (1956), trifluoroacetonitrile (ca. 30 ml.) was condensed into a 250 ml. 3-necked round bottom flask which was cooled in a dry ice-isopropanol bath and fitted with a dry ice condenser. Ammonia (ca. 60 ml.) was then condensed into the flask. The dry ice-isopropanol bath was then removed, and the mixture was allowed to reflux for 1 hour. During the last 15 minutes of reflux time, a bath of cold water was placed around the flask in order to increase the rate of reflux. The dry ice condenser was removed and replaced with a drying tube filled with glass wool. A warm water bath (ca. 55°) was used to enhance the evaporation of excess ammonia. When no gas bubbles were visible in the flask, heating was terminated. The remaining liquid was distilled through a 20 cm. Vigreux column to afford 27.55 g. of trifluoroacetamidine; b.p. 34°-8° C./11 mm. [W. L. Reilly and H. C. Brown, *J. Am. Chem. Soc.* 78, 6032 (1956), b.p. 35°-36° C./11 mm].

PART B — Trifluorothioacetamide

Following the general procedure of Reilly and Brown, W. L. Reilly and H. C. Brown, *J. Am. Chem. Soc.*, 78, 6032 (1956), trifluoroacetamidine (25.51 g.; 0.2278 mole) was dissolved in diethyl ether (80 ml.). Hydrogen sulfide was bubbled into this solution via a sintered glass frit for 15 minutes. The mixture was allowed to stand at ambient temperature for one hour and was then concentrated by rotary evaporation. The residual oil was distilled using a 20 cm. Vigreux column, the major fraction, 15.9 g., being collected at 29° C./1.5–2 mm [W. L. Reilly and H. C. Brown, *J. Am. Chem. Soc.*, 78, 6032 (1956), b.p. 40°/2 mm].

Part C

A solution of p-methoxy-2-bromo-2(p-methoxyphenyl)acetophenone, U.S. Pat. No. 3,560,514, (10.95 g.; 0.0848 mole) trifluoroacetamide (28.4 g.; 0.0840 mole) and acetonitrile (400 ml.) was heated at reflux for 6 hours. The mixture was cooled and concentrated by rotary evaporation. The residue was partitioned with diethyl ether and sodium bicarbonate. The organic layer was washed with water and brine, dried (sodium sulfate) and concentrated by rotary evaporation. This material was chromatographed with 10% ethyl acetate in hexane using a size C pre-packed Merck silica column.

Consolidated fractions were prompted to crystallize in the freezer with scratching. Recrystallization from pentane afforded 8.64 g. (28% yield) of 2-trifluoromethyl-4,5-bis(p-methoxyphenyl)thiazole, m.p. 51°-54°.

Analysis: Calc'd for $C_{18}H_{14}F_3NO_2S$: C, 59.18; H, 3.84; F, 15.62; N, 3.84; S, 8.77. Found: C, 59.34; H, 3.90; F, 15.38; N, 3.84; S, 8.83.

EXAMPLE 2

2-Trifluoromethyl-4,5-bis(p-chlorophenyl)thiazole

Step I — p-Chloro-2-(p-chlorophenyl)acetophenone

The requisite p-chlorophenylacetyl chloride was prepared in the following manner. p-Chlorophenylacetic acid (15 g.; 0.088 mole) and thionyl chloride (31.5 g.; 0.0264 mole) were heated at reflux for 2 hours. Excess thionyl chloride was removed in vacuo to afford the acid chloride which was used without further purification.

Aluminum trichloride (11.75 g.; 0.088 mole) was added portionwise to a stirred mixture of the p-chlorophenylacetyl chloride and chlorobenzene (30 ml.). Following addition, the mixture was allowed to stand for 24 hours. The resulting dark brown paste was scooped out and stirred into a slurry of ice and conc. hydrochloric acid which was then extracted with methylene chloride. The organic extracts were washed with 1 N hydrochloric acid, saturated sodium bicarbonate, saturated sodium chloride; dried over sodium sulfate and concentrated in vacuo. Recrystallization from methanol afforded 16.47 g. (71% yield), m.p. 111.5°–114° C.

Analysis: Calc'd for $C_{14}H_{10}Cl_2O$: C, 63.40; H, 3.77; Cl, 26.79. Found: C, 63.52; H, 3.80; Cl, 26.76.

STEP II —
p-Chloro-2-bromo-2-(p-chlorophenyl)acetophenone

Bromine (2 ml.) was added dropwise to a solution of p-chloro-2-(p-chlorophenyl)acetophenone (10 g.; 0.038 mole), chloroform (50 ml.) and diethyl ether (25 ml.). The mixture was heated at reflux for 0.5 hours and cooled (ca. 20°). Following a thorough washing with saturated sodium bicarbonate, the organic solution was dried over sodium sulfate and concentrated in vacuo. The residue was chromatographed at low pressure through silica gel 60 mesh (230–400) with 5% ethyl acetate in hexane. Recrystallization from hexane afforded 2.69 g.; m.p. 81.5°–83°.

Analysis: Calc'd for $C_{14}H_9BrCl_2O$: C, 48.84; H, 2.62; Br, 23.25; Cl, 20.64. Found: C, 48.75; H, 2.60; Br, 22.33; Cl, 21.10.

Step III —
2-Trifluoromethyl-4,5-bis(p-chlorophenyl)thiazole p-Chloro-2-bromo-2-(p-chlorophenyl)acetophenone (2.69 g.; 0.0078 mole), trifluoromethylthioamide (1.2 g.; 0.00936 mole) (prepared as in the previous example) and acetonitrile (40 ml.) were combined and heated at reflux for 20 hours. The reaction mixture was cooled and then concentrated in vacuo. The residue was partitioned with diethyl ether and saturated sodium bicarbonate, water, and brine; dried (sodium sulfate) and concentrated in vacuo. The residue was triturated with hexane and the hexane solution was decanted and concentrated in vacuo. The residue was chromatographed at low pressure through silica gel 60 (mesh 230–400) with 5% ethanol in hexane. Recrystallization from pentane afforded 0.38 g., m.p. 101°–2° C.

Analysis: Calc'd for $C_{16}H_8Cl_2F_3NS$: C, 51.34; H, 2.14; Cl, 18.98; F, 15.24; N, 3.74; S, 8.56. Found: C, 51.33; H, 2.19; Cl, 19.13; F, 15.43; N, 3.61; S, 8.38.

EXAMPLE 3

2-Trifluoromethyl-4,5-bis(phenyl)thiazole

Following the procedure of Example 2 but substituting phenylacetic acid for p-chlorophenylacetic acid and benzene for chlorobenzene in Step I, 2-trifluoromethyl-4,5-bis(phenyl)thiazole was prepared, m.p. 94°–7° C.

Analysis: Calc'd. for $C_{16}H_{10}F_3NS$: C, 62.95; H, 3.28; N, 4.59; S, 10.49; F, 18.69. Found: C, 62.84; H, 3.47; N, 4.52; S, 10.45; F, 18.34.

EXAMPLE 4

2-Trifluoromethyl-4,5-bis(p-fluorophenyl)thiazole

Following the procedure of Example 2 but substituting p-fluorophenylacetic acid for p-chlorophenylacetic acid and fluorobenzene for chlorobenzene in Step I, 2-trifluoromethyl-4,5-bis(p-fluorophenyl)thiazole can be obtained.

EXAMPLE 5

2-Trifluoromethyl-4,5-bis(p-bromophenyl)thiazole

Following the procedure of Example 2 but substituting p-bromophenylacetic acid for p-chlorophenylacetic acid and bromobenzene for chlorobenzene in Step I, 2-trifluoromethyl-4,5-bis(p-bromophenyl)thiazole can be obtained.

EXAMPLE 6

2-Trifluoromethyl-4,5-bis(p-isopropoxyphenyl)thiazole

Following the procedure of Example 2 but substituting p-isopropoxyphenylacetic acid for p-chlorophenylacetic acid and isopropoxybenzene for chlorobenzene in Step I, 2-trifluoromethyl-4,5-bis(p-isopropoxyphenyl)thiazole can be obtained.

EXAMPLE 7

2-Trifluoromethyl-4,5-bis(p-methoxyphenyl)thiazole. Alternate Procedure for Preparation of 2-trifluoromethyl-4,5-bis(p-methoxyphenyl)thiazole Trifluorothioacetamide was prepared in situ by heating a mixture of trifluoroacetamide (5.0 g.; 0.044 mole), pulverized phosphorus pentasulfide (1.95 g.; 0.0088 mole), and benzene (10 ml.) at reflux for 96 hours. p-Methoxy-2-bromo-2-(p-methoxyphenyl)acetophenone (7.0 g.; 0.021 mole) was added portionwise over 15 minutes. After the mixture was heated at reflux for an additional 1 hour, a solution composed of water (1 ml.) and conc. hydrochloric acid (0.2 ml.) was added. Following an additional hour at reflux, the mixture was cooled and the solvent was removed in vacuo and the residue was made strongly basic with 50% sodium hydroxide. This mixture was heated at 75° for 1 hour, cooled, and then extracted with methylene chloride. The organic extracts were washed with water, saturated sodium chloride, dried over sodium sulfate, and concentrated in vacuo. The resulting crude product was chromatographed at low pressure through silica gel 60 (mesh 230–400) with 10% ethanol in Skelly B hexanes as elutant to yield 2.57 g. of 2-trifluoromethyl-4,5-bis(p-methoxyphenyl)thiazole.

Using this procedure, and replacing p-methoxy-2-bromo-2-(p-methoxyphenyl)acetophenone with (1) 2-bromo-2-phenylacetophenone affords 2-trifluoromethyl-4,5-bis(phenyl)thiazole; (2) p-chloro-2-bromo-2-(p-chlorophenyl)acetophenone affords 2-trifluoromethyl-4,5-bis(p-chlorophenyl)thiazole; (3) p-fluoro-2-bromo-2-(p-fluorophenyl)acetophenone affords 2-trifluoromethyl-4,5-bis(p-fluorophenyl)thiazole; (4) p-isopropoxy-2-bromo-2-(p-isopropoxyphenyl)acetophenone affords (2-trifluoromethyl-4,5-bis)p-isopropoxyphenyl)thiazole; (5) m,p-dimethoxy-2-bromo-2-(m,p-dimethoxyphenyl)acetophenone affords 2-trifluoromethyl-4,5-bis(m,p-dimethoxyphenyl)thiazole.

The above acetophenones are prepared as in Steps I and II of Example 2. (1) Substituting phenylacetic acid for p-chlorophenylacetic acid and benzene for chlorobenzene affords 2-bromo-2-phenylacetophenone. (2) The preparation of p-chloro-2-bromo-2-(p-chlorophenyl)acetophenone is described in Steps I and II of Example 2. (3) Substituting p-fluorophenylacetic acid for p-chlorophenylacetic acid and fluorobenzene for chlorobenzene affords p-fluoro-2-bromo-2-(p-fluorophenyl)acetophenone. (4) Substituting p-isopropoxyphenylacetic acid for p-chlorophenylacetic acid and isopropoxybenzene for chlorobenzene affords p-isopropoxy-2-bromo-2-(p-isopropoxyphenyl)acetophenone. (5) Substituting m,p-dimethoxyphenylacetic acid for p-chlorophenylacetic acid and m,p-dimethoxybenzene for chlorobenzene affords m,p-dimethoxy-2-bromo-2-(m,p-dimethoxyphenyl)acetophenone.

EXAMPLE 8

4,5-Bis(p-methoxyphenyl)thiazole

Part A — Thioformamide

Following the work of Cerecedo and Tolpin [L. R. Cerecedo and J. G. Tolpin, *J. Amer. Chem. Soc.,* 59, 1660 (1937)], formamide (20 g.; 0.444 mole) was covered with diethyl ether (200 ml.) and freshly powdered phosphorus pentasulfide (12 g.; 0.054 mole) was added in several portions with ice water both cooling. The flask was refrigerated at 5°-10° for 72 hours and then allowed to warm to ambient temperature. After being shaken on a shaker apparatus at ambient temperature for 16 hours the ethereal solution of thioformamide was decanted and used in the next step.

Part B — 4,5-Bis(p-methoxyphenyl)thiazole

An ethereal solution of thioformamide (0.153 mole) was concentrated in vacuo at less than 25°. The residue was slurried with acetonitrile (10 ml.) and cooled in an ice water bath. p-Methoxy-2-bromo-2-(p-methoxyphenyl)acetophenone (4.27 g.; 0.0128 mole) was dissolved in acetonitrile (50 ml.) and added via syringe to the above slurry. After stirring for 15 minutes in ice, the flask was refrigerated at 5°-10° for 16 hours. The solution was then stirred at ambient temperature for 70 hours before work up. The solvent was removed in vacuo and the residue was partitioned with ether and saturated sodium bicarbonate solution. The ether layer was washed with saturated sodium bicarbonate solution, water, and saturated sodium chloride solution, dried (sodium sulfate), and concentrated in vacuo. The residue was chromatographed on silica gel 60 at low pressure with 5% ethyl acetate in benzene. Recrystallization from hexane:benzene (11:1) afforded 2.25 g. (59% yield) of 4,5-bis(p-methoxyphenyl)thiazole.

Analysis: Calc'd. for $C_{17}H_{15}NO_2S$: C, 68.69; H, 5.05; N, 4.71; S, 10.77. Found: C, 68.34; H, 5.07; N, 4.58; S, 10.67.

EXAMPLE 9

4,5-Bis(p-methoxyphenyl)-2-thiazoleacetic acid, Lithium Salt 1.6 M n-Butyl lithium in hexane (26.6 ml.) was added by syringe over 10 minutes to a solution of 2-methyl-4,5-bis(p-methoxyphenyl)thiazole (described in U.S. Pat. No. 3,560,514) (11.0 g.; 0.0354 mole) and THF (275 ml.) cooled in a bath of dry ice and isopropyl alcohol. After stirring for 10 minutes the reaction mixture was poured slowly with stirring into a slush of powdered carbon dioxide (500 ml.) and THF (150 ml.). Once the mixture reached ambient temperature it was concentrated by rotary evaporartion. The resulting residue was slurried in diethyl ether and dried (vacuum oven) to afford 12.32 g. (96% yield) of the crude salt. Two g. of this crude material were dissolved in hot acetone. The resulting solution was filtered through a fine sintered glass funnel to remove the haze and allowed to crystallize to afford 1.2 g. of 4,5-bis(p-methoxyphenyl)-2-thiazoleacetic acid, lithium salt.

Analysis: Calc'd. for $C_{19}H_{16}NO_4SLi$: C, 63.16; H, 4.43; N, 3.88; S, 8.86; Li, 1.94. Found: C, 62.61; H, 4.56; N, 3.90; S, 8.74; Li, 1.97.

EXAMPLE 10

4,5-Bis(p-methoxyphenyl)-α,α-dimethyl-2-thiazoleacetic Acid, Sodium salt

A mixture of 4,5-bis(p-methoxyphenyl)-α,α-dimethyl-2-thiazoleacetic acid methyl ester (Example 4) (1.00 g.; 2.52 mm), sodium hydroxide (0.100 g.; 2.52 mm), methanol (50 ml.), and water (5 ml.) was stirred at ambient temperature for 48 hours. The solvents were removed in vacuo to afford 4,5-bis(p-methoxyphenyl)-α,α-dimethyl-2-thiazoleacetic acid, sodium salt.

EXAMPLE 11

4,5-Bis(p-methoxyphenyl)-α,α-dimethyl-2-thiazoleacetic acid, Potassium Salt

A mixture of 4,5-bis(p-methoxyphenyl)-α,α-dimethyl-2-thiazoleacetic acid methyl ester (1.00 g.; 2.52 mm), potassium hydroxide (0.141 g.; 2.52 mm), methanol (50 ml.), and water (5 ml.) was stirred at ambient temperature for 48 hours. The solvents were removed in vacuo to afford 4,5-bis(p-methoxyphenyl)-α,α-dimethyl-2-thiazoleacetic acid, potassium salt.

EXAMPLE 12

4,5-Bis(p-methoxyphenyl)-2-thiazoleacetic acid, Methyl Ester

A solution of 4,5-bis(p-methoxyphenyl)-2-thiazoleacetic acid, lithium salt (8.82 g.; 0.024 mole), methyl iodide (17.4 g.; 0.122 mole) and DMF (100 ml.) was stirred at ambient temperature for 16 hours. The mixture was poured into water (1.5 l.) and extracted with methylene chloride (500 ml.). The organic layer was washed with water (3×1.5 l.), saturated sodium bicarbonate (1.0 l.), water (1.5 l.), dried (sodium sulfate), and concentrated in vacuo. The oily residue was dissolved in acetone and applied directly to a Florisil-packed (340 ml.) gravity column (Florisil previously equilibrated with solvent mixture; 500 ml. packing: 100 ml. solvent). The sample was eluted with 5% acetone in hexane. The recovered product was recrystallized from diethyl ether-pentane to afford 3.32 g. (37% yield) of 4,5-bis(p-methoxyphenyl)-2-thiazoleacetic acid, methyl ester; m.p. 79°-81.5°.

Analysis: Calc'd. for $C_{20}H_{19}NO_4S$: C, 65.04; H, 5.15; N, 3.79; S, 8.67. Found: C, 64.00; H, 5.39; N, 3.58; S, 8.68.

EXAMPLE 13

4,5-Bis(p-methoxyphenyl)-2-thiazole Ethanol

A solution of 4,5-bis(p-methoxyphenyl)-2-thiazoleacetic acid, methyl ester (2.5 g.; 0.0068 mole) and THF (10 ml.) was added dropwise by syringe to an ice cooled slurry of lithium aluminum hydride (0.55 g.; 0.0145 mole) and THF (20 ml.). Stirring was continued for an additional 1.25 hours at ambient temperature. The reaction was quenched by the dropwise addition of water (2 ml. via syringe) and then concentrated by rotary evaporation. The residue was slurried with water, taken to pH 4 with 6 N sulfuric acid, and extracted with methylene chloride. The extracts were washed with water, dried (sodium sulfate), and concentrated by rotary evaporation. The crude mixture was chromatographed (HPLC) with 50% ethyl acetate in benzene through silica gel and then recrystallized from ether-pentane to afford 0.82 g. (35% yield) 4,5-bis(4-methoxyphenyl)-2-thiazole ethanol; m.p. 101°-104° C.

Analysis: Calc'd. for $C_{19}H_{19}NO_3S$: C, 66.86; H, 5.57; N, 4.11; S, 9.38. Found: C, 65.94; H, 5.50; N, 4.07; S, 9.75.

EXAMPLE 14

4,5-Bis(p-methoxyphenyl)-α,α-dimethyl-2-thiazoleacetic acid, Methyl Ester 1.6 M n-Butyl lithium in hexane (10.6 ml.; 0.017 mole) was added dropwise by syringe over 30 minutes to a solution of diisopropylamine (1.48 g.; 0.017 mole) and THF (15 ml.) which was cooled in an ice water bath. Stirring was continued for 15 minutes following addition. The temperature of the solution as lowered by substituting a bath of isopropyl alcohol and dry ice. 4,5-Bis(p-methoxyphenyl)-2-thiazoleacetic acid, methyl ester (5 g.; 0.0136 mole) in THF (15 ml.) was added by syringe over one hour while the temperature of the reaction mixture was maintained below −60°. After stirring for 45 minutes (dry ice bath) methyl iodide (3.83 g.; 0.027 mole) was added by syringe over 5 minutes. Stirring was continued for 15 minutes at which time the solution was allowed to warm to ambient temperature (ca. 20 min.). The reaction mixture was poured into water (500 ml.) and extracted with methylene chloride (2×250 ml.). The organic phase was washed with water (2×500 ml.), 1 N hydrochloric acid (2×250 ml.) and water (1×500 ml.); dried (sodium sulfate) and concentrated by rotary evaporation to afford a crude yield of 4.74 g. This material was taken up in absolute ethanol, treated with DARCO®, filtered and concentrated by rotary evaporation. The residue was chromatographed through two Merck silica gel columns (Size C) with 10% ethyl acetate in benzene. Consolidated fractions afforded 2.69 g. (50% yield) of 4,5-bis(p-methoxyphenyl)-α,α-dimethyl-2-thiazoleacetic acid, methyl ester as an oil.

Analysis: Calc'd. for $C_{22}H_{23}NO_4S$: C, 66.50; H, 5.79; N, 3.53; S, 8.06. Found: C, 66.81; H, 5.93; N, 4.35; S, 8.16.

EXAMPLE 15

4,5-Bis(p-methoxyphenyl)-2-thiazole-α,α-dimethylethanol 4,5-Bis(p-methoxyphenyl)-α,α-dimethyl-2-thiazoleacetic acid, methyl ester (0.81 g.; 0.0020 mole) in THF (5 ml.) was added dropwise by syringe to an ice cooled slurry of lithium aluminum hydride (0.16 g.; 0.0042 mole) and THF (10 ml.). The mixture was stirred for 1 hour at ambient temperature and was then cooled (5°-10°) prior to the dropwise addition of water (0.5 ml.) which quenched the reduction. Solvent was removed by rotary evaporation. The residue was slurried with water (30 ml.), acidified to pH 3 with 6 N sulfuric acid and then extracted with methylene chloride. The extracts were washed with water, dried (sodium sulfate) and concentrated by rotary evaporation to afford a crude oil. This material was triturated with pentane to induce crystallization and then recrystallized from diethyl ether-pentane. The 0.45 g. of product resulting from this procedure had a very broad melting point. The material was dissolved in methylene chloride and washed again with water to remove any inorganic impurities and recrystallized from diethyl ether-pentane to afford 0.19 g. (26% yield) of 4,5-bis(p-methoxyphenyl)-2-thiazole-α,α-dimethylethanol; m.p. 101°-105° C.

Analysis: Calc'd. for $C_{21}H_{23}NO_3S$: C, 68.29; H, 6.23; N, 3.79; S, 8.67. Found: C, 67.68; H, 6.41; N, 3.83; S, 8.48.

EXAMPLE 16

2-Isopropyl-4,5-bis(p-methoxyphenyl)thiazole

A solution of 4,5-bis(p-methoxyphenyl)-α,α-dimethyl-2-thiazoleacetic acid, methyl ester (0.70 g.; 0.0018 mole), 6 N sodium hydroxide (1.6 ml.) and methanol (15 ml.) was stirred at ambient temperature for 16 hours. Methanol was removed by rotary evaporation; the residue was slurried in water (30 ml.) and then adjusted to pH 2 with conc. hydrochloric acid. Decarboxylation occurred while the mixture stirred at ambient temperature for 1.75 hours. The mixture was extracted with methylene chloride. The extracts were dried (sodium sulfate) and concentrated by rotary evaporation to afford 0.59 g. of oily product. The material crystallized slowly at −10° over a period of several days. Recrystallization from pentane afforded 0.19 g. (32% yield) of 2-isopropyl-4,5-bis(p-methoxyphenyl)thiazole; m.p. 61°-65° C.

Analysis: Calc'd. for $C_{20}H_{21}NO_2S$: C, 70.80; H, 6.19; N, 4.13; S, 9.44. Found: C, 70.44; H, 6.16; N, 4.16; S, 9.37.

EXAMPLE 17

4,5-Bis(p-methoxyphenyl)-2-thiazoleacetamide

A three neck flask containing a solution of 4,5-bis(p-methoxyphenyl)-2-thiazoleacetic acid, methyl ester (0.5 g.; 0.00135 mole) and methanol (50 ml.), and fitted with a gas frit and dry ice condenser was cooled in an ice water bath. Ammonia was bubbled into the solution for 15 minutes. After 2 hours of maintaining the ice bath and condenser the entire apparatus (including bath) was wrapped in towels and foil and allowed to stand overnight. The resulting orange solution was concentrated in vacuo. The residue was dissolved in methanol, treated with DARCO® and then concentrated in vacuo. This material was chromatographed through silica gel 60 (mesh 230–400) with 5% isopropyl alcohol in methylene chloride. Recrystallization from diethyl ether-pentane afforded 0.06 g. (13% yield) of product, m.p. 124°-127° C.

Analysis: Calc'd. for $C_{19}H_{18}N_2O_3S$: C, 64.41; H, 5.08; N, 7.91; S, 9.04. Found: C, 64.51; H, 5.51; N, 7.56 S, 9.22.

EXAMPLE 18

Following the procedure of Example 2, but substituting for p-chlorophenylacetic acid the compounds in entry A, and for chlorobenzene, the compounds in entry B, there are obtained in Step III, the products listed in entry C, respectively.

A. m,p-dimethoxyphenylacetic acid
B. chlorobenzene
C. 2-trifluoromethyl-4-(p-chlorophenyl)-5-(m,p-dimethoxyphenyl)thiazole;
A. p-chlorophenylacetic acid
B. o,m-dimethoxybenzene
C. 2-trifluoromethyl-4-(m,p-dimethoxyphenyl)-5-(p-chlorophenyl)thiazole;
A. m,p-dimethoxyphenylacetic acid
B. benzene C. 2-trifluoromethyl-4-phenyl-5-(m,p-dimethoxyphenyl)thiazole;
A. p-methylphenylacetic acid
B. p-t-butoxybenzene
C. 2-trifluoromethyl-4-(p-t-butoxyphenyl)-5-(p-methylphenyl)thiazole;
A. phenylacetic acid
B. ethylbenzene
C. 2-trifluoromethyl-4-(p-ethylphenyl)-5-phenylthiazole.

EXAMPLE 19

Following the procedure of Example 41 of U.S. Pat. No. 3,560,514, but substituting for p-methoxy-2-bromo-2-(p-methoxyphenyl)acetophenone the α-bromoketones afforded as intermediates in Example 18, above, there are prepared the corresponding 2-methyl-4,5-diarylthiazoles.

EXAMPLE 20

Following the sequence established by Examples 9, 12, and 14, but starting with the 2-methyl compounds prepared as in the previous example, there are obtained the corresponding 4,5-diaryl-α,α-dimethyl-2-thiazoleacetic acid, methyl esters.

EXAMPLE 21

Following the procedure of Example 17, but substituting for ammonia the following amines:
bis(2-hydroxyethyl)amine,
ethylamine,
pyrrolidine,
piperidine,
morpholine,
piperazine, and
N-2-hydroxyethyl-N-ethylamine, there are obtained
N,N-bis(2-hydroxyethyl)-4,5-bis(p-methoxyphenyl)-2-thiazoleacetamide,
N-ethyl-4,5-bis(p-methoxyphenyl)-2-thiazoleacetamide,
1-[[4,5-bis(p-methoxyphenyl)-2-thiazolyl]acetyl]pyrrolidine,
1-[[4,5-bis(p-methoxyphenyl)-2-thiazolyl]acetyl]piperidine,
4-[[4,5-bis(p-methoxyphenyl)-2-thiazolyl]acetyl]morpholine,
1-[[4,5-bis(p-methoxyphenyl)-2-thiazolyl]acetyl]piperazine, and
N-2-hydroxyethyl-N-ethyl-4,5-bis(4'-methoxyphenyl)-2-thiazoleacetamide, respectively.

The compounds of the formula II:

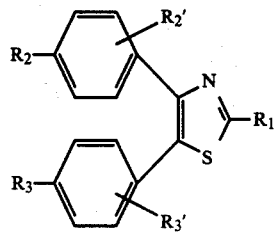

Formula II wherein $R_2$ and $R_3$ are the same or different, and are selected from the group consisting of hydrogen, fluorine, chlorine, bromine, trifluoromethyl, alkoxy of from one to four carbon atoms, inclusive, thioalkoxy of from one to four carbon atoms, inclusive, and alkyl of from one to four carbon atoms, inclusive; $R_{2'}$ and $R_{3'}$ are the same or different and are chosen from the group consisting of hydrogen and alkoxy from one to four carbon atoms, inclusive, with the proviso that when $R_{2'}$ is alkoxy, then $R_2=R_{2'}$ and when $R_{3'}$ is alkoxy then $R_3=R_{3'}$; $R_1$ is selected from the group consisting of hydrogen; alkyl of from one to four carbon atoms, inclusive, trifluoromethyl;

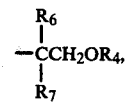

where $R_4$ is hydrogen, alkyl of one to four carbon atoms, inclusive, or

where $R_5$ is alkyl of one to six carbon atoms, inclusive, $R_6$ and $R_7$ are the same or different, and are chosen from the group consisting of hydrogen and alkyl of one to three carbon atoms;

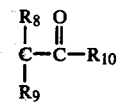

where $R_8$ and $R_9$ are the same or different and are chosen from the group consisting of hydrogen and alkyl from one to three carbon atoms, inclusive, $R_{10}$ is alkoxy of from one to three carbon atoms, inclusive, —OM where M is a pharmaceutically acceptable cation;

where $R_{11}$ and $R_{12}$ are the same or different and are chosen from the group consisting of hydrogen, alkyl of from one to six carbon atoms, inclusive, hydroxyalkyl of from one to six carbon atoms, inclusive, cycloalkyl of from five to seven carbon atoms, inclusive, or take together with the nitrogen atom to which they are attached,

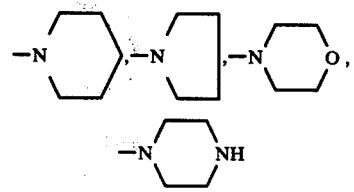

in association with a pharmaceutical carrier. The compositions are useful in vitro and in vivo for reduction of platelet adhesiveness and inhibition of platelet aggregation and preventing or treating disease conditions resulting from increased platelet adhesiveness or platelet aggregation, are prepared in unit dosage form in association with conventional pharmaceutical carrier and administered systemically to humans or animals. The compounds of the formula are also usefully added to in vitro platelet systems. In vitro systems include whole blood and blood kept in blood banks, whole blood as used in heart-lung machines and platelet-rich concentrates. Administration of the compounds to humans or animals provides a method for reducing platelet adhesiveness and inhibiting platelet aggregation.

For in vivo applications the compositions of the present invention are presented for administration to humans and animals in unit dosage forms, such as tablets, capsules, pills, powders, granules, sterile parenteral solutions or suspensions, and oral solutions or suspensions, and oil-in-water and water-in-oil emulsions containing suitable quantities of the compound of Formula II.

For oral administration either solid or fluid unit dosage forms can be prepared. For preparing solid compositions such as tablets, the compound of formula II is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with a syrup vehicle with the aid of a suspending agent such as acacia, tragacanth, methylcellulose and the like.

For parenteral administration, fluid unit dosage forms are prepared utilizing the compound and a sterile vehicle, water being preferred. The compounds, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

For in vitro applications, aqueous solutions are prepared by dissolving a compound of the Formula II in water and adding salt to provide an isotonic solution and buffering to a pH compatible with blood.

Advantageously the composition prepared for parenteral administration can be used when prepared omitting the local anesthetic.

The dosage for humans and animals depends on the blood volume and condition of the subject. A dosage schedule of from about 5 to about 500 mg. per dose, preferably from 10 to 250 mg. administered 1 to 4 times daily is effective for reducing platelet aggregation in the subject. Expressed in terms of weight, the dose can be from 0.3 to 30 mg./kg./day, and preferably from 0.6 to 15 mg./kg./day.

For in vitro, dosage is from 0.0010 to 0.10 micrograms/ml. of whole blood.

The addition of compounds of the Formula II to whole blood provide in vitro applications of the invention such as in the storage of whole blood in blood banks, and whole blood to be used in heart-lung machines. Additionally, whole blood containing a compound of the Formula II can be circulated through organs, e.g., heart and kidneys, which have been removed from a cadaver and prior to transplant.

The compounds of the Formula II can also be used for the preparation of stable platelet-rich plasma concentrates in the same manner as the prostaglandins as disclosed in U.S. Pat. No. 3,629,071 and *Science*, Vol. 175, pp. 536–542 (Feb. 4, 1972).

In vivo applications are the administration to humans and animals to prevent thrombus formation in situations such as following surgery to prevent post-operative thrombosis; to prevent transient cerebral ischemic attacks; and long-term prophylaxis following myocardial infarcts and strokes.

In general a compound of the Formula II is usefully administered prophylactically to humans having a platelet adhesiveness value in excess of 25% [Bygdeman et al., *J. Atheroscler. Res.*, 10, 33–39 (1969)].

In addition to the administration of a compound of the Formula II as the principal active ingredient of compositions for the treatment of the conditions described herein, the said compound can be included with other types of compounds to obtain advantageous combinations of properties. Such combinations include a compound of the Formula II with aspirin, prostaglandins and anti-coagulants such as heparin and dicumerol.

EXAMPLE 22

A lot of 10,000 tablets each containing 50 mg. of 2-trifluoromethyl-4,5-bis(p-methoxyphenyl)thiazole is prepared from the following types and amounts of ingredients:

| | |
|---|---|
| 2-trifluoromethyl-4,5-bis-(p-methoxyphenyl)thiazole | 500 gm. |
| Dicalcium phosphate | 1,500 gm. |
| Methylcellulose, U.S.P. (15 cps.) | 60 gm. |
| Talc | 150 gm. |
| Corn starch | 200 gm. |
| Calcium stearate | 12 gm. |

The dicalcium phosphate and active ingredient are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing thrombus formation at a dose of 1 tablet every four hours following surgery.

EXAMPLE 23

One thousand two-piece hard gelatin capsules, each containing 100 mg. of 2-trifluoromethyl-4,5-bis(p-methoxyphenyl)thiazole are prepared from the following types and amounts of ingredients:

| | |
|---|---|
| 2-trifluoromethyl-4,5-bis-(p-methoxyphenyl)thiazole | 100 gm. |
| Talc | 100 gm. |
| Magnesium stearate | 10 gm. |

The ingredients are mixed well and filled into capsules of the proper size.

Capsules so prepared are useful in preventing further coronary infarcts at a dose of 1 to 4 capsules daily to a patient recovering from a coronary infarct.

EXAMPLE 24

One thousand tablets, each containing 400 mg. of 2-trifluoromethyl-4,5-bis(p-methoxyphenyl)thiazole are made from the following types and amounts of ingredients:

| | |
|---|---|
| 2-trifluoromethyl-4,5-bis-(p-methoxyphenyl)thiazole | 400 gm. |
| Microcrystalline cellulose NF | 120 gm. |
| Starch | 16 gm. |
| Magnesium stearate powder | 4 gm. |

The ingredients are screened and blended together and pressed into 540 mg. tablets.

The tablets are useful to protect against elevated platelet adhesiveness at a dose of 1 tablet daily.

EXAMPLE 25

A sterile preparation suitable for intramuscular injection and containing 50 mg, of 2-trifluoromethyl-4,5-bis(p-methoxyphenyl)thiazole in each milliliter is prepared from the following ingredients:

| | |
|---|---|
| 2-trifluoromethyl-4,5-bis-(p-methoxyphenyl)thiazole | 50 gm. |
| Benzyl benzoate | 200 ml. |
| Methylparaben | 1.5 gm. |
| Propylparaben | 0.5 gm. |
| Cottonseed oil q.s. | 1,000 ml. |

One milliliter of this sterile preparation is injected for prophylactic treatment prior to surgery.

EXAMPLE 26

Aqueous solution

Six hundred ml. of an aqueous solution containing 0.001 mg. of the 2-trifluoromethyl-4,5-bis(p-methoxyphenyl)thiazole per ml. is prepared as follows:

| | |
|---|---|
| 2-trifluoromethyl-4,5-bis-(p-methoxyphenyl)thiazole | 0.6 mg. |
| Sodium chloride | 5,400 mg. |
| Water for injection q.s. | 600 ml. |

The active compound and sodium chloride are dissolved in sufficient water to make 600 ml. and sterile filtered.

The solution is added to whole blood 16 ml./liter for use in a heart-lung machine.

EXAMPLE 27

Following the procedure of the preceding Examples 22 through 26, inclusive, compositions are similarly prepared substituting an equimolar amount each of the compounds of the Formula II prepared in Examples 1 thru 21, inclusive, for the 2-trifluoromethyl-4,5-bis(p-methoxyphenyl)thiazole.

We claim:

1. A compound of the formula

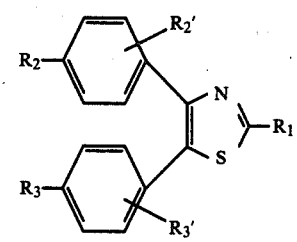

Formula I wherein $R_2$ and $R_3$ are the same or different, and are selected from the group consisting of hydrogen, fluorine, chlorine, bromine, trifluoromethyl, alkoxy of from one to four carbon atoms, inclusive, thioalkoxy of from one to four carbon atoms, inclusive, and alkyl of from one to four carbon atoms, inclusive; $R_{2'}$ and $R_{3'}$ are the same or different and are chosen from the group consisting of hydrogen and alkoxy from one to four carbon atoms, inclusive, with the proviso that when $R_{2'}$ is alkoxy, then $R_2=R_{2'}$ and when $R_{3'}$ is alkoxy then $R_3=R_{3'}$; $R_1$ is selected from the group consisting of hydrogen; trifluoromethyl;

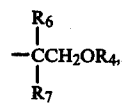

where $R_4$ is hydrogen, alkyl of one to four carbon atoms, inclusive, or

where $R_5$ is alkyl of one to six carbon atoms, inclusive, $R_6$ and $R_7$ are the same or different and are chosen from the group consisting of hydrogen and alkyl of one to three carbon atoms;

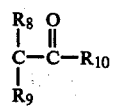

where $R_8$ and $R_9$ are the same or different and are chosen from the group consisting of alkyl from one to three carbon atoms, inclusive, $R_{10}$ is alkoxy of from one to three carbon atoms, inclusive

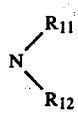

where $R_{11}$ and $R_{12}$ are the same or different and are chosen from the group consisting of hydrogen, alkyl of from one to six carbon atoms, inclusive, hydroxylalkyl of from one to six carbon atoms, inclusive, cycloalkyl of from five to seven carbon atoms, inclusive, or taken together with the nitrogen atom to which they are attached,

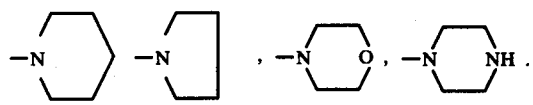

2. A compound of the formula:

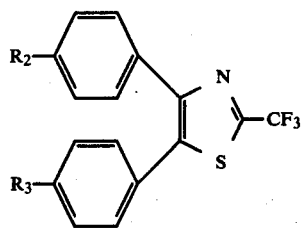

wherein $R_2$ and $R_3$ are the same or different, and are selected from the group consisting of hydrogen, fluorine, chlorine, bromine, trifluoromethyl, alkoxy of from one to four carbon atoms, inclusive, thioalkoxy of from one to four carbon atoms, inclusive, and alkyl of from one to four carbon atoms, inclusive.

3. A compound of the formula:

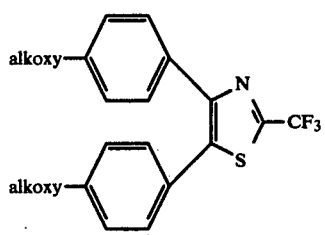

where alkoxy is of one to four carbon atoms.

4. A compound according to claim 1 which is 4,5-bis-(4-methoxyphenyl)-2-thiazole ethanol.

5. A compound according to claim 1 which is 2-thiazoleacetic acid, 4,5-bis(p-methoxyphenyl)-α,α-dimethylmethyl ester.

6. A compound according to claim 1 which is 2-trifluoromethyl-4,5-bis(p-methoxyphenyl)thiazole.

7. A compund according to claim 1 which is 4,5-bis(p-methoxyphenyl)-2-thiazoleacetamide.

8. A process for inhibiting platelet aggregation in vitro comprising the addition of a compound of the formula:

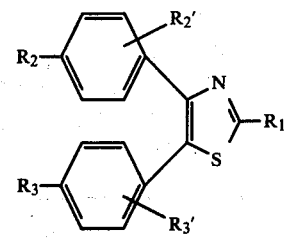

Formula II wherein $R_2$ and $R_3$ are the same or different, and are selected from the group consisting of hydrogen, fluorine, chlorine, bromine, trifluoromethyl, alkoxy of from one to four carbon atoms, inclusive, thioalkoxy of from one to four carbon atoms, inclusive, and alkyl of from one to four carbon atoms, inclusive; $R_{2'}$ and $R_{3'}$ are the same or different and are chosen from the group consisting of hydrogen and alkoxy from one to four carbon atoms, inclusive, with the proviso that when $R_{2'}$ is alkoxy, then $R_2=R_{2'}$ and when $R_{3'}$ is alkoxy then $R_3=R_{3'}$; $R_1$ is selected from the group consisting of hydrogen; alkyl of from one to four carbon atoms, inclusive, trifluoromethyl;

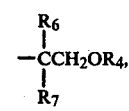

where $R_4$ is hydrogen, alkyl of one to four carbon atoms, inclusive, or

where $R_5$ is akyl of one to six carbon atoms, includive, $R_6$ and $R_7$ are the same or different, and are chosen from the group consisting of hydrogen and alkyl of one to three carbon atoms;

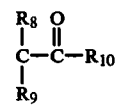

where $R_8$ and $R_9$ are the same or different and are chosen from the group consisting of hydrogen and alkyl from one to three carbon atoms, inclusive, $R_{10}$ is alkoxy of from one to three carbon atoms, inclusive, —OM where M is a pharmaceutically acceptable cation;

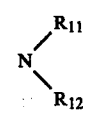

where $R_{11}$ and $R_{12}$ are the same or different and are chosen from the group consisting of hydrogen, alkyl of from one to six carbon atoms, inclusive, hydroxyalkyl of from one to six carbon atoms, inclusive, cycloalkyl of from five to seven carbon atoms, inclusive, or taken together with the nitrogen atom to which they are attached,

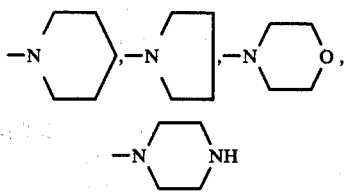

in association with a pharmaceutical carrier. The compositions are useful in vitro and in vivo for reduction of platelet adhesiveness and inhibition of platelet aggregation and preventing or treating disease conditions resulting from increased platelet adhesiveness or platelet aggregation.

9. The process of claim 16 wherein the amount of the compound added is from about 0.0010 to 0.10 micrograms per ml. of whole blood.

10. A process according to claim 8 wherein the compound selected is 2-trifluoromethyl-4,5-bis(p-methoxyphenyl)thiazole.

11. A process according to claim 8 wherein the compound selected is 4,5-bis(p-methoxyphenyl)-2-thiazoleacetamide.

12. A process for prophylactic or therapeutic treatment comprising the systemic administration to a human or animal of a compound of the formula:

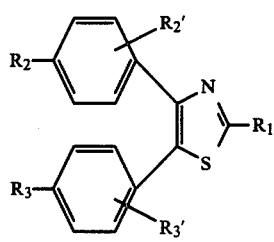

Formula II wherein $R_2$ and $R_3$ are the same or different, and are selected from the group consisting of hydrogen, fluorine, chlorine, bromine, trifluoromethyl, alkoxy of from one to four carbon atoms, inclusive, thioalkoxy of from one to four carbon atoms, inclusive, and alkyl of from one to four carbon atoms, inclusive; $R_2'$ and $R_3'$ are the same or different and are chosen from the group consisting of hydrogen and alkoxy from one to four carbon atoms, inclusive, with the proviso tht when $R_2'$ is alkoxy, then $R_2=R_2'$ and when $R_3'$ is alkoxy then $R_3=R_3'$; $R_1$ is selected from the group consisting of hydrogen; alkyl of from one to four carbon atoms, inclusive, trifluoromethyl;

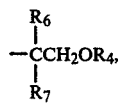

where $R_4$ is hydrogen, alkyl of one to four carbon atoms, inclusive, or

where $R_5$ is alkyl of one to six carbon atoms, inclusive, $R_6$ and $R_7$ are the same or different, and are chosen from the group consisting of hydrogen and alkyl of one to three carbon atoms;

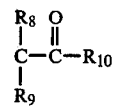

where $R_8$ and $R_9$ are the same or different and are chosen from the group consisting of hydrogen and alkyl from one to three carbon atoms, inclusive, $R_{10}$ is alkoxy of from one to three carbon atoms, inclusive, —Om where M is a pharmaceuticaly acceptable cation;

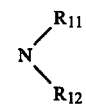

where $R_{11}$ and $R_{12}$ are the same or different and are chosen from the group consisting of hydrogen, alkyl of from one to six carbon atoms, inclusive, hydroxyalkyl of from one to six carbon atoms, inclusive, cycloalkyl of from five to seven carbon atoms, inclusive, or taken together with the nitrogen atom to which they are attached,

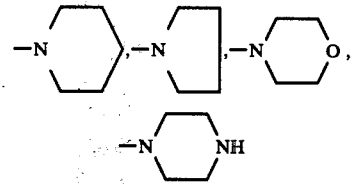

in association with a pharmaceutical carrier. The compositions are useful in vitro and in vivo for reduction of platelet adhesiveness and inhibition of platelet aggregation and preventing or treating disease conditions resulting from increased platelet adhesiveness or platelet aggregation.

13. The process of claim 12 wherein the amount of the compound administered is from about 5 to 500 mg.

14. A process according to claim 12 wherein the compound selected is 2-trifluoromethyl-4,5-bis(p-methoxyphenyl)thiazole.

15. A process according to claim 12 wherein the compound selected is 4,5-bis(p-methoxyphenyl)-2-thiazoleacetamide.

16. A therapeutic composition for reducing platelet-adhesiveness comprising from 5 mg. to 500 gm. of a compound of the formula:

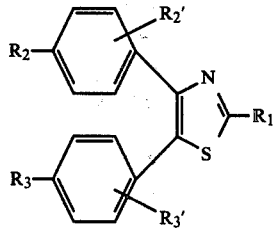

Formula II wherein $R_2$ and $R_3$ are the same or different, and are selected from the group consisting of hydrogen, fluorine, chlorine, bromine, trifluoromethyl, alkoxy of from one to four carbon atoms, inclusive, thioalkoxy of from one to four carbon atoms, inclusive, and alkyl of from one to four carbon atoms, inclusive; $R_{2'}$ and $R_{3'}$ are the same or different and are chosen from the group consisting of hydrogen and alkoxy from one to four carbon atoms, inclusive, with the proviso that when $R_{2'}$ is alkoxy, then $R_2=R_{2'}$ and when $R_{3'}$ is alkoxy then $R_3=R_{3'}$; $R_1$ is selected from the group consisting of hydrogen; alkyl of from one to four carbon atoms, inclusive, trifluoromethyl;

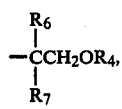

where $R_4$ is hydrogen, alkyl of one to four carbon atoms, inclusive, or

where $R_5$ is alkyl of one to six carbon atoms, inclusive, $R_6$ and $R_7$ are the same or different, and are chosen from the group consisting of hydrgoen and alkyl of one to three carbon atoms;

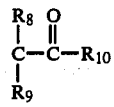

where $R_8$ and $R_9$ are the same or different and are chosen from the group consisting of hydrogen and alkyl from one to three carbon atoms, inclusive, $R_{10}$ is alkoxy of from one to three carbon atoms, inclusive, —OM where M is a pharmaceutically accetable cation;

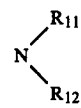

where $R_{11}$ and $R_{12}$ are the same or different and are chosen from the group consisting of hydrogen, alkyl of from one to six carbon atoms, inclusive, hydroxyalkyl of from one to six carbon atoms inclusive, cycloalkyl of from five to seven carbon atoms, inclusive, or taken together with the nitrogen atom to which they are attached,

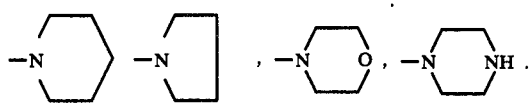

17. A composition according to claim 16 wherein the compound selected is 4,5-bis(p-methoxyphenyl)-thiazole.

18. A composition according to claim 16 wherein the compound selected is 4,5-bis(p-methoxyphenyl)-2-thiazoleacetamide.

* * * * *

UNITED STATES PATENT OFFICE
CERTIFICATE OF CORRECTION

Reexamination Certificate for
Patent No. BI 4,168,315                 Dated   18 September 1979

Inventor(s)   R. H. Rynbrandt and E. E. Nishizawa

It is certified that error appears in the above-identified patent and that said Letters Patent is hereby corrected as shown below:

Column 3, line 18, "thioalkyl" should read -- thioalkoxy --.

Column 4, lines 12-21; Column 5, lines 43-53; and Column 7, lines 1-12: The formula should appear as follows:

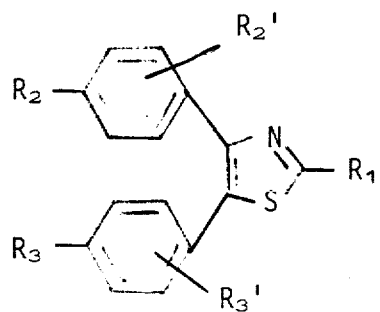

UNITED STATES PATENT OFFICE
CERTIFICATE OF CORRECTION

Reexamination Certificate for
Patent No. B1 4,168,315        Dated     18 September 1979

Inventor(s) R. H. Rynbrandt and E. E. Nishizawa

It is certified that error appears in the above-identified patent and that said Letters Patent is hereby corrected as shown below:

Column 6, lines 29-36, that portion of the formula should read

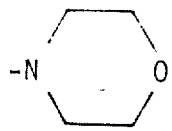

Signed and Sealed this

Twenty-fourth Day of October, 1989

Attest:

DONALD J. QUIGG

Attesting Officer        Commissioner of Patents and Trademarks

REEXAMINATION CERTIFICATE (353rd)

United States Patent [19]
Rynbrandt et al.

[11] B1 4,168,315
[45] Certificate Issued May 28, 1985

[54] *NOVEL* DIANISYL THIAZOLE COMPOUND, COMPOSITIONS AND METHOD OF ANTITHROMBOTIC TREATMENT

[75] Inventors: Ronald H. Rynbrandt, Portage; Edward E. Nishizawa, Schoolcraft Township, Kalamazoo County, both of Mich.

[73] Assignee: The Upjohn Company, Kalamazoo, Mich.

Reexamination Request:
No. 90/000,466, Nov. 7, 1983

Reexamination Certificate for:
Patent No.: 4,168,315
Issued: Sep. 18, 1979
Appl. No.: 837,083
Filed: Sep. 28, 1977

[51] Int. Cl.$^3$ .............. C07D 277/20; A61K 31/425
[52] U.S. Cl. .................... 424/270; 424/248.5; 424/250; 424/267; 424/270; 548/201; 548/202; 548/203; 548/204
[58] Field of Search ............... 548/201, 202, 203; 424/270, 271, 250, 274, 248.5, 267

[56] References Cited

U.S. PATENT DOCUMENTS

| | | | |
|---|---|---|---|
| 3,279,918 | 10/1966 | Cassies et al. | 548/202 |
| 3,558,644 | 1/1971 | Lednicer | 260/302 |
| 3,560,514 | 2/1971 | Lednicer | 260/302 |
| 3,707,475 | 12/1972 | Lombardino | 260/309 |
| 3,851,063 | 11/1974 | Shen et al. | 548/335 |
| 4,099,011 | 7/1978 | Möller et al. | 424/270 |
| 4,282,234 | 8/1981 | Durant et al. | 424/270 |

FOREIGN PATENT DOCUMENTS

29875/67 5/1969 Australia .

OTHER PUBLICATIONS

Lee et al., J. Pharm. & Exp. Ther. 95 71-78 (1949).
J. G. Lombardino & E. H. Wiseman, J. Med. Chem. 17:1182 (1974) "Preparation and Antiinflammatory Activity of Some Nonacidic Trisubstituted Imidazoles".
E. H. Wiseman, H. M. McIlhenny & J. W. Bettis, J. Pharm. Sci. 64:1469 (1975) "Flumizole, A New Nonsteroidal Anti-Inflammatory Agent".

*Primary Examiner*—Nicholas S. Rizzo

[57] ABSTRACT

Novel compounds of Formula I:

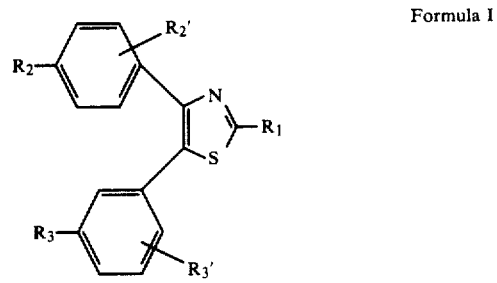

Formula I in association with a pharmaceutical carrier. The compositions are useful in vitro and in vivo for reduction of platelet adhesiveness and inhibition of platelet aggregation and preventing or treating disease conditions resulting from increased platelet adhesiveness or platelet aggregation.

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, line 5 to Column 3, line 23:

SCHEME I

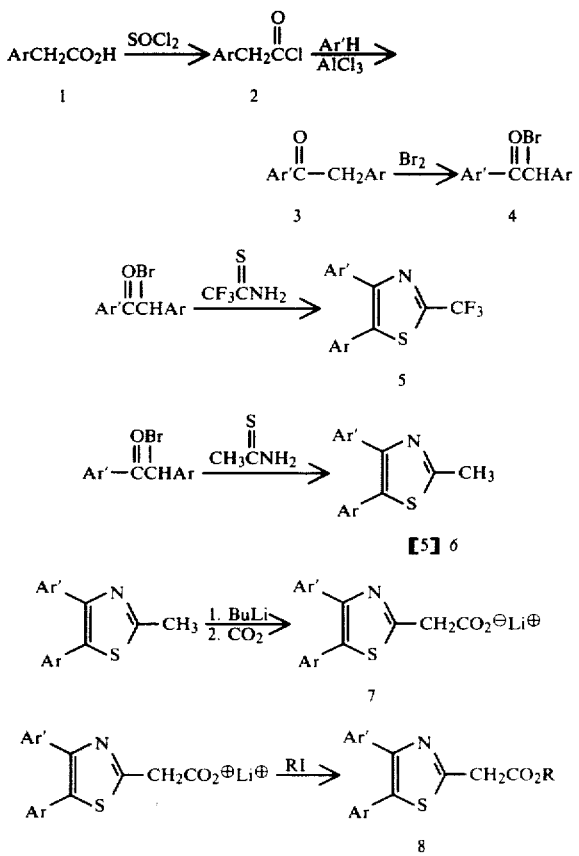

Column 9, lines 42–68:

EXAMPLE 9

4,5-Bis (p-methoxyphenyl)-2-thiazoleacetic acid, Lithium Salt 1.6 M n-Butyl lithium in hexane (26.6 ml.) was added by syringe over 10 minutes to a solution of 2-methyl-4,5-bis(p-methoxyphenyl)thiazole (described in U.S. Pat. No. 3,560,514) (11.0 g.; 0.0354 mole) and THF (275 ml.) cooled in a bath of dry ice and isopropyl alcohol. After stirring for 10 minutes the reaction mixture was poured slowly with stirring into a slush of powdered carbon dioxide (500 ml.) and THF (150 ml.). Once the mixture reached ambient temperature it was concentrated by rotary *evaporation* [evaporartion]. The resulting residue was slurried in diethyl ether and dried (vacuum oven) to afford 12.32 g. (96% yield) of the crude salt.

Two g. of this crude material were dissolved in hot acetone. The resulting solution was filtered through a fine sintered glass funnel to remove the haze and allowed to crystallize to afford 1.2 g. of 4,5-bis(p-methoxyphenyl)-2-thiazoleacetic acid, lithium salt.

Column 11, lines 8–40:

EXAMPLE 14

4,5-Bis (p-methoxyphenyl)-α,α-dimethyl-2-thiazoleacetic acid, Methyl Ester 1.6 M n-Butyl lithium in hexane (10.6 ml.; 0.017 mole) was added dropwise by syringe over 30 minutes to a solution of diisopropylamine (1.48 g.; 0.017 mole) and THF (15 ml.) which was cooled in an ice water bath. Stirring was continued for 15 minutes following addition. The temperature of the solution [as] *was* lowered by substituting a bath of isopropyl alcohol and dry ice. 4,5-Bis(p-methoxyphenyl)-2-thiazoleacetic acid, methyl ester (5 g.; 0.0136 mole) in THF (15 ml.) was added by syringe over one hour while the temperature of the reaction mixture was maintained below −60°. After stirring for 45 minutes (dry ice bath) methyl iodide (3.83 g.; 0.027 mole) was added by syringe over 5 minutes. Stirring was continued for 15 minutes at which time the solution was allowed to warm to ambient temperature (ca. 20 min.). The reaction mixture was poured into water (500 ml.) and extracted with methylene chloride (2×250 ml.). The organic phase was washed with water (2×500 ml.), 1 N hydrochloric acid (2×250 ml.) and water (1×500 ml.); dried (sodium sulfate) and concentrated by rotary evaporation to afford a crude yield of 4.74 g. This material was taken up in absolute ethanol, treated with DARCO®, filtered and concentrated by rotary evaporation. The residue was chromatographed through two Merck silica gel columns (Size C) with 10% ethyl acetate in benzene. Consolidated fractions afforded 2.69 g. (50% yield) of 4,5-bis(p-methoxyphenyl)-α,α-dimethyl-2-thiazoleacetic acid, methyl ester as an oil.

Column 17, lines 40–53:

EXAMPLE 25

A sterile preparation suitable for intramuscular injection and containing 50 mg [,] *of* 2-trifluoromethyl-4,5-bis(p-methoxyphenyl)thiazole in each milliliter is prepared from the following ingredients:

| | |
|---|---|
| 2-trifluoromethyl-4,5-bis-(p-methoxyphenyl)thiazole | 50 gm. |
| Benzyl benzoate | 200 ml. |
| Methylparaben | 1.5 gm. |
| Propylparaben | 0.5 gm. |
| Cottonseed oil q.s. | 1,000 ml. |

AS A RESULT OF REEXAMINATION, IT HAS BEEN DETERMINED THAT:

The patentability of claims 2 and 3 is confirmed.

Claims 5, 7 and 18 are cancelled.

Claims 1, 8, 9, 12 and 16 are determined to be patentable as amended.

Claims 4, 6, 10, 11, 13–15 and 17, dependent on an amended claim, are determined to be patentable.

1. A compound of the formula

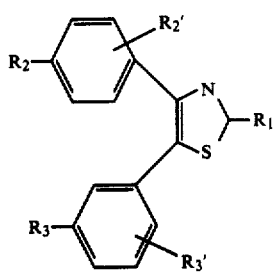

Formula I wherein R₂ and R₃ are the same or different, and are selected from the group consisting of hydrogen, fluorine, chlorine, bromine, trifluoromethyl, alkoxy of from one to four carbon atoms, inclusive, thioalkyl of from one to four carbon atoms, inclusive, and alkyl of from one to four carbon atoms, inclusive; R₂' and R₃' are the same or different and are chosen from the group consisting of hydrogen and alkoxy of from one to four carbon atoms, inclusive, with the proviso that when R₂' is alkoxy, then R₂=R₂' and when R₃' is alkoxy then R₃=R₃'; R₁ is selected from the group consisting of [hydrogen;] trifluoromethyl[;] and

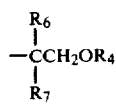

wherein R₄ is hydrogen, alkyl of one to four carbon atoms, inclusive, or

wherein R₅ is alkyl of one to six carbon atoms, inclusive, R₆ and R₇ are the same or different and are chosen from the group consisting of hydrogen and alkyl of one to three carbon atoms[,]

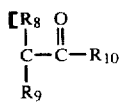

[where R₈ and R₉ are the same or different and are chosen from the group consisting of alkyl of from one to three carbon atoms, inclusive, R₁₀ is alkoxy of from one to three carbon atoms, inclusive]

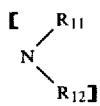

[wherein R₁₁ and R₁₂ are the same or different and are chosen from the group consisting of hydrogen, alkyl of from one to six carbon atoms, inclusive, cycloalkyl of from five to seven carbon atoms, inclusive, or taken together with the nitrogen atom to which they are attached,

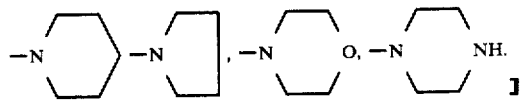

]

8. A process for inhibiting platelet aggregation in vitro comprising the addition of a compound of the formula:

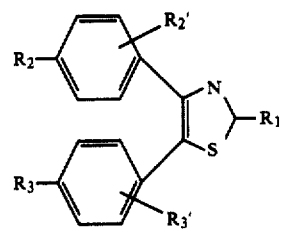

Formula II wherein R₂ and R₃ are the same or different, and are selected from the group consisting of hydrogen, fluorine, chlorine, bromine, trifluoromethyl, alkoxy of from one to four carbon atoms, inclusive, thioalkoxy of from one to four carbon atoms, inclusive, and alkyl of from one to four carbon atoms, inclusive; R₂' and R₃' are the same or different and are chosen from the group consisting of hydrogen and alkoxy of from one to four carbon atoms, inclusive, with the proviso that when R₂' is alkoxy, then R₂=R₂' and when R₃' is alkoxy then R₃=R₃'; R₁ is selected from the group consisting of hydrogen; alkyl of from one to four carbon atoms, inclusive, trifluoromethyl;

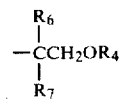

wherein R₄ is hydrogen, alkyl of one to four carbon atoms, inclusive, or

where R₅ is alkyl of one to six carbon atoms, [includive] inclusive, R₆ and R₇ are the same or different, and are chosen from the group consisting of hydrogen and alkyl of one to three carbon atoms;

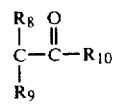

where R₈ and R₉ are the same or different and are chosen from the group consisting of hydrogen and alkyl of from one to three carbon atoms inclusive, R₁₀ is alkoxy of from one to three carbon atoms, inclusive, —OM where M is a pharaceutically acceptable cation;

where $R_{11}$ and $R_{12}$ are the same or different and are chosen from the group consisting of hydrogen, alkyl of from one to six carbon atoms, inclusive, hydroxyalkyl of from one to six carbon atoms, inclusive, cycloalkyl of from five to seven carbon atoms, inclusive, or taken together with the nitrogen atom to which they are attached,

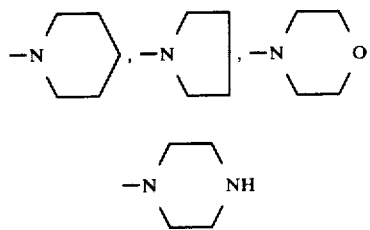

in association with a pharmaceutical carrier. [The compositions are useful in vitro for reduction of platelet adhesiveness and inhibition of platelet aggregation and preventing or treating disease conditions resulting from increased platelet adhesiveness or platelet aggregation.]

9. The process of claim [16] 8 wherein the amount of the compound added is from about 0.0010 to 0.10 micrograms per ml. of whole blood.

12. A process for prophylactic or therapeutic treatment of disease conditions resulting from increased platelet adhesiveness or platelet aggregation comprising the systemic administration to a human or animal of a compound of the formula:

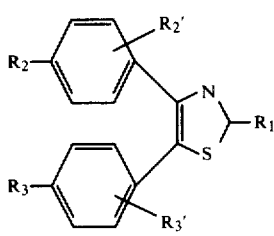

Formula II wherein $R_2$ and $R_3$ are the same or different, and are selected from the group consisting of hydrogen, fluorine, chlorine, bromine, trifluoromethyl, alkoxy of from one to four carbon atoms, inclusive, thioalkoxy of from one to four carbon atoms, inclusive, and alkyl of from one to four carbon atoms, inclusive; $R_2'$ and $R_3'$ are the same or different and are chosen from the group consisting of hydrogen and alkoxy of from one to four carbon atoms, inclusive, with the proviso [tht] that when $R_2'$ is alkoxy, then $R_2 = R_2'$ and when $R_3'$ is alkoxy then $R_3 = R_3'$; $R_1$ is selected from the group consisting of hydrogen; alkyl of from one to four carbon atoms, inclusive, trifluoromethyl;

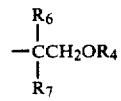

wherein $R_4$ is hydrogen, alkyl of one to four carbon atoms, inclusive, or

where $R_5$ is alkyl of one to six carbon atoms, inclusive, $R_6$ and $R_7$ are the same or different, and are chosen from the group consisting of hydrogen and alkyl of one to three carbon atoms,

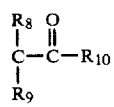

where $R_8$ and $R_9$ are the same or different and are chosen from the group consisting of hydrogen and alkyl of from one to three carbon atoms, inclusive, $R_{10}$ is alkoxy of from one to three carbon atoms, inclusive, [—Om] —OM where M is a pharmaceutically acceptable cation;

where $R_{11}$ and $R_{12}$ are the same or different and are chosen from the group consisting of hydrogen, alkyl of from one to six carbon atoms, inclusive, hydroxyalkyl of from one to six carbon atoms, inclusive, cycloalkyl of from five to seven carbon atoms, inclusive, or taken together with the nitrogen atom to which they are attached,

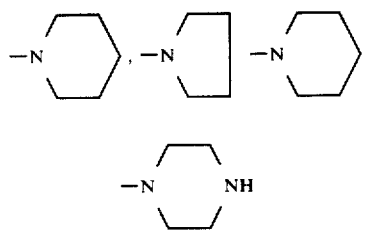

in association with a pharmaceutical carrier. [The compositions are useful in vitro and in vivo for reduction of platelet adhesiveness and inhibition of platelet aggregation and preventing or treating disease conditions resulting from increased platelet adhesiveness or platelet aggregation.]

16. A therapeutic composition for reducing platelet-adhesiveness comprising from 5 mg. to 500 gm. of a compound of the formula:

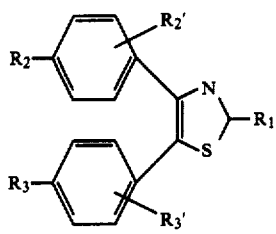

Formula II wherein $R_2$ and $R_3$ are the same or different, and are selected from the group consisting of hydrogen, fluorine, chlorine, bromine, trifluoromethyl, alkoxy of from one to four carbon atoms, inclusive, thioalkoxy of from one to four carbon atoms, inclusive, and alkyl of from one to four carbon atoms, inclusive; $R_2'$ and $R_3'$ are the same or different and are chosen from the group consisting of hydrogen and alkoxy of from one to four carbon atoms, inclusive, with the proviso that when $R_2'$ is alkoxy, then $R_2 = R_2'$ and when $R_3'$ is alkoxy then $R_3 = R_3'$; $R_1$ is selected from the group consisting of hydrogen; alkyl of from one to four carbon atoms, inclusive, trifluoromethyl[;] and

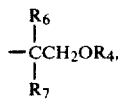

wherein $R_4$ is hydrogen, alkyl of one to four carbon atoms, inclusive, or

where $R_5$ is alkyl of one to six carbon atoms, *inclusive*, $R_6$ and $R_7$ are the same or different, and are chosen from the group consisting of hydrogen and alkyl of one to three carbon atoms;

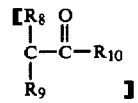

[where $R_8$ and $R_9$ are the same or different and are chosen from the group consisting of hydrogen and alkyl from one to three carbon atoms inclusive, $R_{10}$ is alkoxy of from one to three carbon atoms, inclusive, —OM where M is a pharaceutically acceptable cation;]

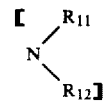

[where $R_{11}$ and $R_{12}$ are the same or different and are chosen from the group consisting of hydrogen, alkyl of from one to six carbon atoms, inclusive, hydroxyalkyl of from one to six carbon atoms, inclusive, cycloalkoxy of from five to seven carbon atoms, inclusive, or taken together with the nitrogen atom to which they are attached,]

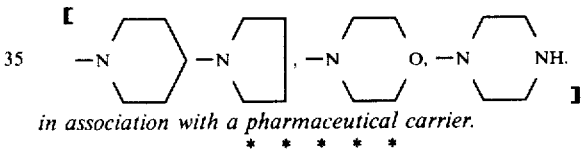

*in association with a pharmaceutical carrier.*

* * * * *